United States Patent [19]

Kreidl et al.

[11] Patent Number: 4,614,824

[45] Date of Patent: Sep. 30, 1986

[54] NOVEL APOVINCAMINIC ACID DERIVATIVES

[75] Inventors: János Kreidl; László Czibula; György Visky; Mária Farkas née Kirják; Judit Mészáros née Brill; Dóra Groó; Éva Pálosi; Egon Kárpáti; László Szporny, all of Budapest, Hungary

[73] Assignee: Richter Gedeon Vegyeszeti Gyar R.T., Budapest, Hungary

[21] Appl. No.: 754,671

[22] Filed: Jul. 11, 1985

Related U.S. Application Data

[63] Continuation of Ser. No. 508,661, Jun. 28, 1983, abandoned.

[30] Foreign Application Priority Data

Jun. 30, 1982 [HU] Hungary ................... 2128/82

[51] Int. Cl.⁴ ................. C07D 461/00; A61K 31/435
[52] U.S. Cl. ................................................. 546/51
[58] Field of Search ......................... 546/51; 514/283

[56] References Cited

U.S. PATENT DOCUMENTS

| | | | |
|---|---|---|---|
| 3,770,724 | 11/1973 | Warnant et al. | 546/51 X |
| 3,987,177 | 10/1976 | Giudicelli et al. | 546/51 X |
| 4,035,370 | 7/1977 | Lörincz et al. | 424/256 X |
| 4,316,028 | 2/1982 | Katsube et al. | 546/51 |
| 4,400,514 | 8/1983 | Szántay et al. | 546/51 |

FOREIGN PATENT DOCUMENTS

| | | | |
|---|---|---|---|
| 0052238 | 5/1982 | European Pat. Off. | 546/51 |
| 2062619 | 5/1981 | United Kingdom | 546/51 |

OTHER PUBLICATIONS

Giudicelli, et al., Chemical Abstracts, vol. 84, 135922g (1976).
Gallo Molino, Chemical Abstracts. vol. 94, 30986j (1981).
Galzigna, et al., Chemical Abstracts, vol. 95, 25376b (1981).

*Primary Examiner*—Donald G. Daus
*Assistant Examiner*—Diana G. Rivers
*Attorney, Agent, or Firm*—Keil & Weinkauf

[57] ABSTRACT

The invention relates to new racemic and optically active apovincaminic acid derivatives of the general formula (I)

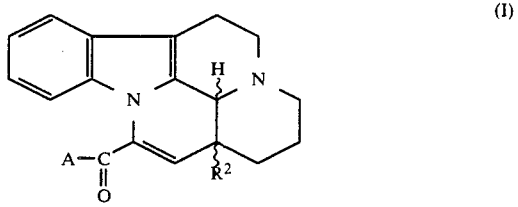

wherein

A is hydroxyl, halogen or a group $-O-(CH_2)_n-OR^1$ or $-OMe$, in which $R^1$ is alkyl having from one to 6 carbon atoms, n is an integer between 2 and 6, Me is an alkali metal, $R^2$ stands for an alkyl group having from one to 6 carbon atoms, which may be identical with or different from $R^1$, and the hydrogen in the 3-position and the $R^2$ group have an $\alpha,\alpha$- and/or $\beta,\beta$- or $\alpha,\beta$- and/or $\beta,\alpha$-configuration, and pharmaceutically acceptable acid addition salts thereof, which are pharmaceutically active, e.g. show antihypoxial activity or are potent peripheral vasodilators. Their preparation and pharmaceutical composition containing them are also within the scope of the invention.

1 Claim, No Drawings

NOVEL APOVINCAMINIC ACID DERIVATIVES

This application is a continuation of application Ser. No. 508,661, filed on June 28, 1983, now abandoned.

The invention relates to new apovincaminic acid derivatives, a process for their preparation and pharmaceutical compositions containing them. More particularly, the invention concerns new racemic or optically active apovincaminic acid derivatives of the formula (I)

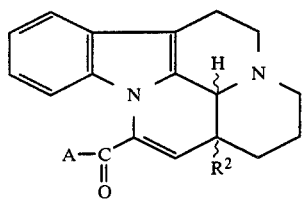

(I)

wherein
A is hydroxyl, halogen or a group —O—(CH$_2$)$_n$—OR$^1$ or —OMe, in which
R$^1$ is alkyl having from 1 to 6 carbon atoms,
n is an integer from 2 to 6,
Me is an alkali metal,
R$^2$ stands for an alkyl group having from 1 to 6 carbon atoms, which may be identical with or different from R$^1$,
and the hydrogen in the 3-position and the R$^2$ group have an α,α- and/or β,β- or α,β- and/or β,α-configuration, and pharmaceutically acceptable acid addition salts thereof.

The invention further relates to a process for the preparation of compounds of the formula (I) and pharmaceutically acceptable acid addition salts thereof by reacting apovincamine derivatives of the formula (II),

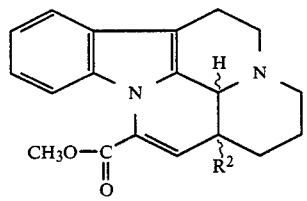

(II)

wherein R$^2$ and the configuration of the 3-hydrogen and R$^2$ are the same as defined above, or optical antipodes, racemates or acid addition salts thereof, with glycol monoalkylether derivatives of the formula (III), R$^1$O—(CH$_2$)$_n$—Y   (III)

wherein
R$^1$ and n have the same meaning as defined above, and
Y is hydroxyl,
in the presence of an alkali metal monoglycolate of the latter compound.

Alternatively, a compound of the formula (II), in which R$^2$ and the configuration of the hydrogen in the 3-position and R$^2$ are the same as defined above, or an optical antipode, racemate or acid addition salt thereof may first be hydrolysed to yield a corresponding compound of the formula (I), in which A is hydroxyl or an optical antipode, racemate or an acid addition salt thereof, formed with an inorganic acid, which is then treated with a halogenating agent and, if desired, a compound of the formula (I) obtained, in which A stands for halogen, R$^2$ and the configuration of the 3-hydrogen and R$^2$ are as defined above, or an optical antipode, racemate or acid addition salt thereof is reacted with a disjunct glycol monoalkylether derivative of the formula (III), in which
R$^1$ and n are as defined above, and
Y is hydroxyl or an —OMe group, in which
Me is an alkali metal atom.

According to a further alternative a compound of the formula (I), in which A is hydroxyl, R$^2$ and the configuration of the 3-hydrogen and R$^2$ are the same as defined above, or an optical antipode, racemate or an acid addition salt thereof formed with an inorganic acid is treated with a base and, if desired, an apovincaminic acid derivative of the formula (I) obtained, in which A represents a group —OMe, in which Me is an alkali metal, R$^2$ and the configuration of the 3-hydrogen and R$^2$ are as defined above, or an optical antipode, racemate or acid addition salt thereof, is reacted with a glycol monoalkylether derivative of the formula (III), in which R$^1$ and n are as defined above and Y is halogen.

If desired, the apovincaminic acid derivatives of the formula (I) or optical antipodes or racemates thereof are treated with a pharmaceutically acceptable acid to form a corresponding acid addition salt.

The new compounds of the formula (I) are biologically active and particularly those in which A represents an —O—(CH$_2$)$_n$—OR$^1$ group show valuable pharmaceutical activity. Compounds of the formula (I), in which A is a group —O—(CH$_2$)$_n$—OR$^1$ and the configuration of the 3-hydrogen and R$^2$ is α,α and/or β,β, possess a significant antihypoxial activity, while those in which the configuration of the 3-hydrogen and R$^2$ is α,β and/or β,α are potent peripheral vasodilators. The pharmaceutical compositions containing compounds of the formula (I), in which A and R$^2$ are as defined above, as an active ingredient or pharmaceutically acceptable acid addition salts thereof are also within the scope of the invention.

In the general formulae R$^1$ and R$^2$ as an alkyl group having from 1 to 6 carbon atoms represent straight or branched chained alkyl groups, thus methyl, ethyl, n-propyl, isopropyl, n-butyl, sec-butyl, tert-butyl, n-pentyl, isopentyl, n-hexyl, isohexyl groups. Y as a halogen atom stands for fluorine, chlorine, bromine or iodine. Me may stand for any alkali metal atom, e.g. sodium or potassium atom; and the integer n is 2, 3, 4, 5 or 6.

The starting compounds of the general formula (II) are prepared e.g. as described in the German Patent Specification No. 1,244,794 for example by dehydrating vincamine.

Starting compounds of the general formula (III) in which Y is hydroxyl are commercially available products.

The compounds of the general formula (III) in which Y stands for a halogen atom are prepared from a disjunct glycol monoalkylether of the formula R$^1$O—(CH$_2$)$_n$—OH and thionyl chloride as described in the Org. Synth. Coll. Vol. I. p. 371 (1932).

The apovincamine derivatives of the general formula (II) are reacted with the disjunct glycol monoalkylether derivatives of the general formula (III) generally in an excess amount of the latter compounds as a solvent, but any inert organic solvent, preferably an aromatic hydrocarbon, such as benzene, toluene or xylene, may equally be used for this purpose. The reaction is preferably carried out at the boiling temperature of the reaction mixture. The alkali metal monoglycolates of the compounds of the general formula (III) used in a catalytic amount [compounds of the general formula (III) in which $R^1$ and n are as hereinabove defined and Y represents an —OMe group, in which Me is an alkali metal] are prepared by reacting a compound of the general formula (III), in which Y is hydroxyl, $R^1$ and n are as defined above, with an alkali metal, e.g. sodium, potassium, lithium or an alkali metal alcoholate, e.g. sodium methylate, potassium tert-butylate, sodium tert-butylate, or an alkali metal hydride, e.g. sodium hydride, potassium hydride.

According to another alternative in a compound of the general formula (III), which is present in an excess amount, and in which $R^1$ and n are as defined above, a catalytic amount of an alkali metal or an alkali metal alcoholate is dissolved, and a compound of the general formula (II) is added to the solution obtained.

The apovincamine derivatives of the general formula (II) are hydrolysed in the presence of a base in a manner known per se. As a base for example an inorganic basic compound, preferably an alkali metal hydroxide, e.g. sodium hydroxide, is employed and the solvent preferably is an alkanol having from 1 to 6 carbon atoms, e.g. methanol, in an aqueous solution.

The apovincaminic acid derivatives of the general formula (I), in which A stands for hydroxyl, $R^2$ and the configuration of $R^2$ and the 3-hydrogen are as defined above, are halogenated for example with thionyl chloride, thionyl bromide, oxalyl chloride, etc. Halogenation is performed in an organic solvent inert under the reaction conditions, for example a halogenated aliphatic or aromatic hydrocarbon, such as chloroform, carbon tetrachloride, dichloroethane, chlorobenzene, etc. If desired, a catalyst, such as dimethyl formamide or pyridine, may facilitate the halogenation.

The reaction of the apovincaminic acid derivatives of the general formula (I), wherein A is halogen, $R^2$ and the configuration of $R^2$ and the hydrogen in the 3-position are as defined above, with the glycol monoalkylether derivatives of the general formula (III), in which Y is hydroxyl, $R^1$ and n are as defined above, is preferably accomplished in an excess amount of the compound of the general formula (III) as a solvent. But as a solvent an inert organic solvent may equally be employed. Such solvents include halogenated hydrocarbons, such as chloroform, dichloromethane or dichloroethane, or cyclic ethers, such as dioxane or tetrahydrofurane.

The apovincaminic acid derivatives of the general formula (I), in which A is halogen, $R^2$ and the configuration of the 3-hydrogen and $R^2$ have the same meaning as defined above, are generally reacted with the glycol monoalkylether derivatives of the general formula (III), in which Y is a group —OMe, wherein Me is an alkali metal, $R^1$ and n are as defined above, in an inert organic solvent, preferably in a cyclic ether, such as dioxane or tetrahydrofurane.

As a basis in the reaction of the apovincaminic acid derivatives of the general formula (I), in which A is hydroxyl and $R^2$ and the configuration of the 3-hydrogen and $R^2$ are as defined above, with a base, any inorganic base, preferably an alkali metal hydroxide, such as potassium or sodium hydroxide, or an alkali metal carbonate, e.g. sodium or potassium carbonate, may be used. The reaction is for example carried out by reacting the apovincamine derivative with the solid alkali metal hydroxide, preferably taken in an equimolar amount, in an inert organic solvent, for example an alkanol having from one to 6 carbon atoms, such as methanol, or an aromatic hydrocarbon, such as benzene or toluene, and evaporating the reaction mixture to dryness by azeotropic distillation. The solid residue, which is the corresponding alkali metal salt, is reacted with the glycol monoalkylether derivative of the general formula (III), in which $R^1$ and n are as defined above, in an inert organic solvent, preferably a cyclic ether, such as tetrahydrofurane, or an aromatic hydrocarbon, e.g. benzene or toluene.

Alternatively, an apovincaminic acid derivative of the general formula (I), in which A is hydroxyl, $R^2$ and the configuration of $R^2$ and the 3-hydrogen are as defined above, is admixed with a suitable base, preferably sodium or potassium carbonate in an equimolar amount, preferably in the absence of water, in an aprotic dipolar solvent, such as hexamethyl phosphoric acid triamide, dimethyl formamide or methyl ethyl ketone, and the glycol monoalkylether derivative of the general formula (III) is added to the solution obtained, which contains the apovincaminic acid alkali metal salt solution.

The compounds of the general formula (I) can be converted into their pharmaceutically acceptable acid addition salts by reacting with suitable acids.

The suitable acids include inorganic acids, such as hydrogen halides, e.g. hydrochloric acid, hydrogen bromide, sulfuric acid, phosphoric acid, nitric acid, perhalogen acids, e.g. perchloric acid, etc.; organic carboxylic acids, e.g. formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-aminobenzoic acid, p-hydroxy-benzoic acid, p-amino-salicylic acid, etc.; alkylsulfonic acids, such as methanesulfonic acid, ethane-sulfonic acid, etc.; cycloaliphatic sulfonic acids, such as cyclohexylsulfonic acid; arylsulfonic acids, such as p-toluene-sulfonic acid, naphthylsulfonic acid, sulfanylic acid, etc.; amino acids, such as asparaginic acid, glutaminic acid, N-acetyl-asparaginic acid, N-acetyl-glutaric acid, etc.

The salts are prepared in an inert organic solvent, e.g. an aliphatic alcohol having from 1 to 6 carbon atoms, by dissolving a racemic or optically active compound of the general formula (I) in the solvent, and subsequently adding a suitable acid or a solution thereof with the above solvent, until the pH of the mixture becomes slightly acidic (about pH 5–6). The precipitated acid addition salt is then separated from the reaction mixture by a suitable method, for example filtration.

The racemic compounds of the general formula (I) can be resolved in a known manner but one can start also from optically active compounds of the general formula (II). Generally, if racemic compounds of the general formula (I) are to be prepared, racemic starting compounds of the general formula (II) are employed, while optically active compounds of the general formula (I) are generally prepared by starting from optically active compounds of the general formula (II).

The optically active compounds of the general formula (I) or the racemates thereof, prepared according to the invention as well as their acid addition salts can be further purified for example by recrystallization. The solvents used for recrystallization are selected depending on the solubility and the crystallizability of the compound to be recrystallized.

The antihypoxial activity of the compounds of the general formula (I), in which A is a group —O—($CH_2$)$_n$—$OR^1$, in which $R^1$, n and $R^2$, and the configuration of $R^2$ and the 3-hydrogen are as defined above, was tested by the following methods.

1. Hypobaricus hypoxia [Baumel T. et al.: Proc. Soc. Exp. Biol. (NY) 132, 629 (1969)].

Male and female CFLP mice (n=10) weighing 24 to 26 g. were treated with a 50 mg./kg. intraperitoneal dose of the test materials, after fasting for 16 hours. After treatment the animals were placed into an exsiccator, in which the pressure was reduced to 73.3 kPa in 25 seconds and the survival time of the animals was measured under this pressure. The animals living 100% longer than the average of the group treated with placebo are considered protected.

2. Asphyxial anoxia [Caillard C. et al.: Life Sci. 16, 1607 (1975)].

Mice were treated as described under point 1 above. 30 minutes after treatment the animals were placed into hermetically sealed 100-ml. bottles and the survival time was measured.

Animals living 30% longer than the average of the control group treated with placebo were considered protected.

3. Normobaric hypoxia

Mice were treated as described under point 1 above. 30 minutes after treatment the animals were placed into a 3-lit glass cylinder through which a mixture of 96% nitrogen and 4% oxygen was passed at a speed of 3 lit./min. The gas mixture could leave the system through a hole on the opposite wall of the cylinder. The interval between placing the animals into the cylinders and ceasing of the respiratory movement was determined. The animals living twice as long than the average of the control group treated with solvent only were considered protected. In the following Table the average of the survival times (±SE) and the % of the protected animals are given.

cording to the invention was longer; moreover, certain animals entirely survived the hypoxial conditions.

The compounds of the formula (I) can be formulated as pharmaceutical compositions for parenteral or enteral administration. Such compositions are prepared by admixing the active compounds with one or more solid or liquid carrier and/or further additives conventionally used in the preparation of pharmaceutical compositions. As a carrier for example water, gelatine, lactose, milk sugar, starch, pectine, magnesium stearate, stearic acid, talc, vegetable oils, such as peanut oil, olive oil, etc. can be employed. The pharmaceutical compositions can be formulated for example in a solid (e.g. globular or angular tablets, dragées, capsules, such as hard gelatine capsules, pills, suppositories, etc.) or liquid (e.g. oily or aqueous solutions, suspensions, emulsions, syrups, soft gelatine capsules, injectable oily or aqueous solutions or suspensions, etc.) form. The amount of the solid carrier can be varied within a wide range, but preferably is between 25 mg. and 1 g. If desired, the compositions may contain further, conventional pharmaceutical additives, such as preservatives, stabilizing agents, wetting agents, emulsifying agents, salts to adjust the osmosis pressure, buffers, flavouring and aroma agents, etc. Further pharmaceutically active compounds which do not show a synergistic effect with the compounds according to the invention may also be present. The dose units are selected depending on the route of administration. The pharmaceutical compositions are prepared by the conventional techniques of pharmaceutical industry. The ingredients are for example screened, admixed, granulated and subsequently pressed or dissolved in a suitable solvent. Thereafter the compositions may be subjected to further conventional treatments, e.g. sterilization.

Further details of the invention will now be illustrated by the following Examples, which do not limit our invention.

EXAMPLE 1

(+)-Cis-apovincaminic acid (3α,16α)

TABLE

| Material | Asphyxial anoxia | | Hypobaricus hypoxia | | Normobaricus hypoxia | |
|---|---|---|---|---|---|---|
| | survival time min/aver. ±SE/ | % of protected animals | survival time min/aver. ±SE/ | % of protected animals | survival time min/aver. ±SE/ | % of protected animals |
| Placebo | 15.2 ± 1.04$^x$ | — | 64.5 ± 3.53$^{xx}$ | — | 5.0 ± 0.39$^{xxx}$ | — |
| Vincamine | 20.1 ± 1.09 | 40 | 129.8 ± 3.18 | 40 | 7.1 ± 1.12 | 0 |
| /+/-cis-apovincaminic acid methoxyethylester | 22.4 ± 1.44 | 70 | 185.0 ± 30.52 | 60 | 13.5 ± 0.73 | 90 |

$^x$limit time: 19.8 min
$^{xx}$limit time: 129 sec
$^{xxx}$limit time: 15.0 min From the data set forth in the Table it can be seen that for example (+)-cis-apovincaminic acid methoxyethyl ester prepared according to the invention has a positive influence on the oxygen metabolism of the brain in comparison with other compounds known to have a similar effect and placebo, respectively. The compounds according to the invention increase the applicability of oxygen and in this way in an anoxial state inhibit the damage of the brain tissue. The animal tests were carried out under serious hypoxial conditions induced in different manners which are lethal under normal conditions. The tests indicate that the survival of the test animals pretreated with the compounds ac- 50.5 g. of (+)-cis-apovincamine(3α,16α) are refluxed in a mixture of 400 ml. of methyl alcohol, 38 g. of solid sodium hydroxide and 25 ml. of water for 30 minutes. Methyl alcohol is distilled off and the residue is dissolved in 300 ml. of water and is then acidified to pH 6.50 with a 1 molar aqueous citric acid solution. The precipitated desired compound is filtered, washed with altogether 150 ml. of distilled water in three portions and is subsequently dried. 46.5 g. of the desired compound are obtained as a snow-white microcrystalline product.

Yield: 95.8%

Melting point: 260° to 261° C. (decomp.).
$[\alpha]_D^{20} = +69°$ [c=1, methanol/ammonia].

EXAMPLE 2

(+)-Cis-apovincaminic acid chloride hydrochloride-(3α,16α)

64.5 g. of (+)-cis-apovincaminic acid(3α,16α) prepared according to Example 1 are suspended in 250 ml. of dichloroethane. To the suspension 0.1 ml. of dimethyl formamide are added followed by the dropwise addition of 26.2 g. of thionyl chloride. The reaction mixture is stirred at 40° C. for 3 hours, evaporated to dryness in vacuo, and the oily evaporation residue is treated with 200 ml. of cyclohexane. The crystals obtained are filtered off, washed with two 30-ml. portions of cyclohexane and dried. 70 g. of the desired compound are obtained.

Melting point: 184° to 186° C.

The product can be used in the subsequent reaction steps without further purification.

EXAMPLE 3

(+)-Cis-apovincaminic acid methoxyethyl ester(3α,16α)

1.8 g. of 80% sodium hydride are dissolved in 50 ml. of ethyleneglycol monomethyl ether and 11.3 g. of (+)-cis-apovincaminic acid chloride hydrochloride prepared according to Example 2 are added to the solution. The reaction mixture is stirred at room temperature for 3 hours, 50 ml. of water are added and the mixture is extracted with 100 ml. of dichloromethane. The phases are separated and the aqueous phase is shaken with a further 50-ml. portion of dichloromethane. The combined dichloromethane phases are dried with solid, anhydrous magnesium sulfate, filtered and the filtrate is evaporated to dryness. The oily residue obtained is treated with three 50-ml. portions of n-hexane. 12.5 g. of the desired compound are obtained, which are then crystallized from 20 ml. of diisopropyl ether to yield 10.8 g. of the aimed compound.

Yield: 80%.
Melting point: 102° to 103° C.
$[\alpha]_D^{20} = +128.9°$ (c=1, chloroform).

EXAMPLE 4

(+)-Trans-apovincaminic acid methoxyethylester(3α,16β)hydrochloride

In 100 ml. of dry ethyleneglycol monomethylether 0.2 g. of potassium metal are dissolved and 8.4 g. (0.025 moles) of (+)-trans-apovincaminic acid methylester(-3α,16β) are added to the solution. The solution is stirred at 60° C. for 30 minutes, whereupon the solvent is distilled off under a pressure of 20 to 25 mmHg. in 1 hour. The residue is cooled to room temperature, 50 ml. of water are added and the pH of the mixture is adjusted to 2 with a 1:1 mixture of hydrochloric acid and water. The mixture containing a crystalline material is heated until the crystals are dissolved and it is then slowly cooled to induce crystallization. The mixture is allowed to stand at 0° C. for 4 hours, filtered, washed by covering with two 30-ml. portions of cold water and dried. 9.4 g. of the crude aimed compound are obtained, which is then recrystallized from 60 ml. of water. 8.5 g. of the aimed compound are obtained.

Yield: 82%.
Melting point: 237° to 238° C.
$[\alpha]_D^{20} = +147.3°$ (c=1, chloroform).

EXAMPLE 5

(+)-Trans-apovincaminic acid(3α,16β)

33.6 g. of (+)-trans-apovincamine(3α,16β) and 250 ml. of methyl alcohol are refluxed in a solution of 25 g. of solid sodium hydroxide in 25 ml. of water for 45 minutes. The methyl alcohol is then distilled off, the residue is dissolved in 250 ml. of water and acidified to pH 6.60 with a 1 molar citric acid solution. The precipitated aimed compound is filtered off, washed with altogether 160 ml. of distilled water in four portions and dried. 30.5 g. of the aimed compound are obtained as a snow-white amorphous material.

Yield: 94.1%.
Melting point: 208° to 210° C. (decomp.)
$[\alpha]_D^{20} = +136.1°$ (c=1, dimethyl formamide).

EXAMPLE 6

(+)-Trans-apovincaminic acid chloride hydrochloride

To 100 ml. of thionyl chloride 40 g. (0.125 moles) of (+)-trans-apovincaminic acid(3α,16β) prepared according to Example 5 are added. The mixture is stirred at 60° C. for 3 hours while the solid material is entirely dissolved. The solution is cooled to 20° C., and 25 ml. of diisopropyl ether are added whereupon a yellowish, sticky material is precipitated. The liquid is decanted, triturated with 150 ml. of diisopropyl ether, filtered, washed by pulpifying with two 50-ml. portions of diisopropyl ether and dried. 45 g. of the aimed compound are obtained as a slightly yellowish amorphous powder.

Yield: 96%.
Melting point: 171° to 172° C.

EXAMPLE 7

(+)-Trans-apovincaminic acid methoxyethyl ester(3α,16β)hydrochloride 9.4 g. (0.025 moles) of (+)-trans-apovincaminic acid chloride hydrochloride prepared according to Example 6 are added to 100 ml. of dry ethyleneglycol monomethylether, the mixture is stirred at 60° C. for one hour and the solvent is eliminated by distillation in vacuo. The residue is dissolved in 60 ml. of hot water, the solution is decoloured while hot, filtered and the filtrate is allowed to cool to yield a crystalline precipitate. The precipitated crystals are filtered off, washed by covering with two 10-ml. portions of cold water and dried. 9.2 g. of a crude product are obtained, which is then dissolved in 60 ml. of hot water, decolourized with activated carbon, filtered and the filtrate is cooled to induce crystallization. 8.3 g. of the aimed compound are obtained.

Yield: 80%.
Melting point: 237° to 238° C.
$[\alpha]_D^{20} = +147°$ (c=1, chloroform).

EXAMPLE 8

(−)-Cis-apovincaminic acid methoxyethyl ester(3α,16α)

16.1 g. of (+)-cis-apovincaminic acid prepared according to Example 1 are dissolved in 160 ml. of dry hexamethylphosphoric acid triamide, to the solution 8.3 g. of finely powdered, dry solid potassium carbonate are added under exclusion of water, followed by the addition of 8.3 g. of methoxyethyl bromide at room temperature, in 15 minutes. The mixture is stirred at room temperature, then poured onto 300 ml. of ice water and extracted with altogether 200 ml. of benzene, in four portions. The combined benzene solutions are dried, decolourized with activated carbon, evaporated to dryness in vacuo and the residue is crystallized from 30 ml. of diisopropylether. 14.3 g. of the aimed compound are obtained.

Yield: 75%.

Melting point: 102° to 103° C.

$[\alpha]_D^{20} = +128.2°$ (c=1, chloroform).

We claim:

1. Racemic and optically active apovincaminic acid compounds of the formula

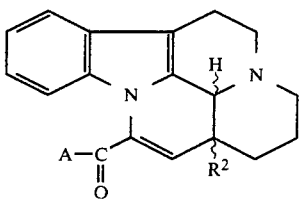

wherein
A is $-O-(CH_2)_n-OR^1$,
in which
R$^1$ is alkyl of 1 to 6 carbon atoms,
n is 2,
R$^2$ stands for an alkyl group of 1 to 6 carbon atoms, which may be identical or different from R$^1$,
and the hydrogen in the 3-position and the R$^2$ group have an $\alpha,\alpha$- and/or $\beta,\beta$- or $\alpha,\beta$- and/or $\beta,\alpha$-configuration, and pharmaceutically acceptable acid addition salts thereof.

* * * * *